(12) United States Patent
Schrank et al.

(10) Patent No.: US 9,543,245 B2
(45) Date of Patent: Jan. 10, 2017

(54) SEMICONDUCTOR SENSOR DEVICE AND METHOD OF PRODUCING A SEMICONDUCTOR SENSOR DEVICE

(71) Applicant: ams AG, Unterpremstaetten (AT)

(72) Inventors: Franz Schrank, Graz (AT); Martin Schrems, Eggersdorf (AT)

(73) Assignee: ams AG, Unterpremstaetten (AT)

( * ) Notice: Subject to any disclaimer, the term of this patent is extended or adjusted under 35 U.S.C. 154(b) by 0 days.

(21) Appl. No.: 14/441,165

(22) PCT Filed: Sep. 23, 2013

(86) PCT No.: PCT/EP2013/069705
§ 371 (c)(1),
(2) Date: May 6, 2015

(87) PCT Pub. No.: WO2014/072114
PCT Pub. Date: May 15, 2014

(65) Prior Publication Data
US 2015/0287674 A1 Oct. 8, 2015

(30) Foreign Application Priority Data
Nov. 7, 2012 (EP) .................................... 12191647

(51) Int. Cl.
*G01N 27/12* (2006.01)
*H01L 23/528* (2006.01)
(Continued)

(52) U.S. Cl.
CPC ........... *H01L 23/528* (2013.01); *G01N 27/128* (2013.01); *H01L 21/50* (2013.01);
(Continued)

(58) Field of Classification Search
CPC .. H01L 23/528; H01L 23/315; H01L 23/3135; H01L 21/565; G01N 27/128; G01N 27/129
USPC ......................................................... 257/414
See application file for complete search history.

(56) References Cited

U.S. PATENT DOCUMENTS 7,495,300 B2 2/2009 Gardner et al.
7,659,612 B2 2/2010 Hembree et al.
(Continued)

FOREIGN PATENT DOCUMENTS

EP 1775259 A1 4/2007
GB 2303710 A 2/1997
(Continued)

*Primary Examiner* — Christine Enad
(74) *Attorney, Agent, or Firm* — McDermott Will & Emery LLP

(57) ABSTRACT

The semiconductor device comprises a substrate (1) of semiconductor material with a front side (4) and an opposite rear side (7), a wiring layer (5) at the front side (4), a further wiring layer (8) at the rear side (7), and a through-substrate via (3) connecting the wiring layer (5) and the further wiring layer (8). A hot plate (24) is arranged on or in the substrate, and a sensor layer (21) is arranged in the vicinity of the hot plate. A mold compound (14) is arranged on the rear side (7) above the substrate (1), a cavity (17) is formed in the mold compound (14) to accommodate the sensor layer (21), and the cavity (17) is covered with a membrane (15).

9 Claims, 1 Drawing Sheet

(51) Int. Cl.
- *H01L 21/50* (2006.01)
- *H01L 23/00* (2006.01)
- *H01L 21/56* (2006.01)
- *H01L 23/31* (2006.01)

(52) U.S. Cl.
CPC .......... *H01L 21/565* (2013.01); *H01L 23/315* (2013.01); *H01L 23/3135* (2013.01); *H01L 24/94* (2013.01); *H01L 24/97* (2013.01); H01L 23/3121 (2013.01); H01L 2224/02371 (2013.01); H01L 2224/02372 (2013.01); H01L 2224/0401 (2013.01); H01L 2224/04042 (2013.01); H01L 2224/0557 (2013.01); H01L 2224/05569 (2013.01); H01L 2224/06181 (2013.01); H01L 2224/13022 (2013.01); H01L 2224/13024 (2013.01); H01L 2224/14181 (2013.01); H01L 2224/16145 (2013.01); H01L 2224/16225 (2013.01); H01L 2224/48145 (2013.01); H01L 2224/48227 (2013.01); H01L 2224/73257 (2013.01); H01L 2224/94 (2013.01); H01L 2224/97 (2013.01); H01L 2924/00014 (2013.01); H01L 2924/12042 (2013.01); H01L 2924/14 (2013.01); H01L 2924/15311 (2013.01); H01L 2924/181 (2013.01); H01L 2924/18161 (2013.01)

(56) References Cited

U.S. PATENT DOCUMENTS 8,049,287 B2   11/2011   Combi et al.
2001/0042684 A1*  11/2001  Essalik .............. G01N 27/4073 204/426
2003/0173233 A1*  9/2003  Vincent .................. G01N 27/40 205/793
2005/0086998 A1*  4/2005  Qin ...................... B01D 19/0031 73/31.07
2006/0154401 A1   7/2006  Gardner et al.
2007/0045515 A1   3/2007  Farnworth et al.
2007/0272553 A1*  11/2007  Gambert .............. G01N 27/404 204/431
2009/0256216 A1   10/2009  Kierse
2010/0230766 A1   9/2010  Elian et al.
2011/0013788 A1*  1/2011  Izuchi .................. H04R 19/016 381/174
2012/0006099 A1*  1/2012  Kajiyama .......... G01N 27/4071 73/31.05
2012/0056312 A1   3/2012  Pagaila et al.
2012/0280594 A1*  11/2012  Chen ...................... H03H 3/007 310/313 R
2012/0313209 A1*  12/2012  Oganesian ........ H01L 27/14618 257/443
2014/0134607 A1*  5/2014  Lin ...................... G01N 27/327 435/5
2016/0104806 A1*  4/2016  Thrush ................ H01L 27/1462 257/434

FOREIGN PATENT DOCUMENTS

| JP | 2001337063 A | 12/2001 |
| KR | 20100036853 A | 4/2010 |
| TW | I290358 B | 11/2007 |

\* cited by examiner

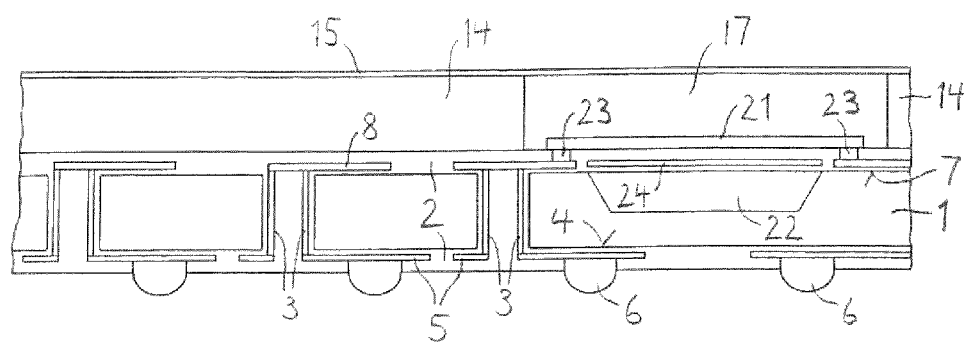

SEMICONDUCTOR SENSOR DEVICE AND METHOD OF PRODUCING A SEMICONDUCTOR SENSOR DEVICE

BACKGROUND OF THE INVENTION

U.S. Pat. No. 7,495,300 B2 discloses a gas-sensing semiconductor device on silicon, comprising a resistive heater made of tungsten embedded in a thin silicon oxide layer that is formed over a recess of the silicon substrate. The device can be monolithically integrated with a circuitry using a CMOS process.

U.S. Pat. No. 7,659,612 B2 discloses semiconductor components comprising through wire interconnects, which are partially encapsulated by a polymer layer and include redistribution conductors and pads electrically connected with substrate contacts. A method for fabricating the components can include a film assisted molding process for forming the polymer layer on the wafer level. Following the film assisted molding process the components are singulated. The semiconductor components can be used to fabricate stacked systems.

TW 1290358 B discloses a packaging for a micro gas sensor, which is mounted in a receptacle of a carrier and is provided with electric connections. The receptacle is closed by a filter component, which is fixed to the carrier above the sensor and comprises a structure net and a thin film.

KR 101034647 B1 describes a wafer-level packaging for a gas sensor. A substrate comprising cavities containing sensors and support units is covered with a further substrate, which is provided with a cavity and an infrared filter. The substrates are bonded by means of a metal solder layer.

US 2012/0056312 A1 describes a production method for a stack of semiconductor wafers comprising through silicon vias and a plurality of dies mounted in cavities between the vias. An encapsulant is deposited over the dies. Interconnect structures are formed above the encapsulant and are electrically connected to the vias. When the wafers are provided with the encapsulant and the interconnect structures, they are mounted on top of each other.

US 2007/0045515 A1 discloses microelectronic imaging devices having integrated circuits and image sensors on opposite sides of a substrate, which is provided with through-substrate vias. Standoffs formed from a cover material support a transmissive element including glass, which is attached to the standoffs by attachment elements including adhesive layers and protects a microlens array and other features from contamination. The cover material can include a photoresist or another selectively removable substance.

US 2009/0256216 A1 discloses a wafer-level chip scale package of a sensor with a substrate comprising ICs, through-silicon vias and a protective encapsulant layer covering the top surface. Above a cavity accommodating the sensor, a cap is arranged either flush with the encapsulant layer or partially covered by the encapsulant layer.

US 2006/0154401 A1 discloses gas-sensing semiconducting devices including a gas-sensitive layer and a heater arranged in the vicinity of the gas-sensitive layer.

GB 2303710 A discloses a gas sensor with a gas-permeable membrane formed from polytetrafluoroethylene.

JP 2001-337063 A discloses a gas sensor inserted in a recessed part of a housing with bumps of the gas sensing part turned downward. Leads are connected by heating the bumps while the sensor main body is lowered towards the leads.

EP 1775259 A1 discloses a wafer level package for devices that may include two different sensors, in particular a pressure sensor and an accelerometer.

US 2010/0230766 A1 discloses a sensor device comprising an encapsulating mold material with polytetrafluoroethylene used as a coating material.

SUMMARY OF THE INVENTION

The semiconductor device that is produced in wafer-level package comprises a substrate of semiconductor material with a front side and an opposite rear side, a wiring layer at the front side, a further wiring layer at the rear side, and a through-substrate via connecting the wiring layer and the further wiring layer. A hot plate is arranged in or on the substrate at the rear side. A sensor layer is arranged in the vicinity of the hot plate and is electrically connected with the further wiring layer. A mold compound is arranged on the rear side and is covered with a membrane. The mold compound and the membrane form a cavity accommodating the sensor layer.

In an embodiment the hot plate is part of the further wiring layer.

In a further embodiment, the sensor layer is arranged above the substrate, and the hot plate is arranged between the substrate and the sensor layer.

In a further embodiment the hot plate is arranged above a recess of the substrate.

In a further embodiment the membrane is impermeable to liquids and permeable to a gas.

In a further embodiment the membrane is polytetrafluoroethylene or expanded polytetrafluoroethylene.

The method of producing the semiconductor devices in wafer-level package comprises the steps of forming a plurality of semiconductor devices on a substrate of semiconductor material with a front side and an opposite rear side, arranging a wiring layer at the front side, arranging a further wiring layer at the rear side, forming through-substrate vias connecting the wiring layer and the further wiring layer, arranging a plurality of hot plates and sensor layers in or above the substrate at the rear side, arranging and structuring a mold compound on the rear side above the substrate to form a plurality of cavities for the accommodation of the sensor layers, and covering the cavities with a membrane.

In a variant of the method, the membrane is impermeable to liquids and permeable to a gas.

In a further variant of the method, the membrane is formed from polytetrafluoroethylene or expanded polytetrafluoroethylene.

In a further variant of the method, the membrane is temporarily covered with a protection film. This may be favorable to enable a solder reflow process without poisoning the sensor layers.

In a further variant of the method, the membrane is glued to the mold compound.

In a further variant of the method, the membrane is ultrasonically welded to the mold compound.

In a further variant of the method, the mold compound is applied in a structured fashion by use of a film assisted molding process.

The following is a detailed description of examples of the semiconductor sensor device and the method of production in conjunction with the appended FIGURE.

BRIEF DESCRIPTION OF THE DRAWINGS

FIG. 1 is a cross section of an embodiment of the semiconductor sensor device.

DETAILED DESCRIPTION

The substrate 1 is provided with a dielectric 2, through-substrate vias 3, a wiring layer 5 embedded in the dielectric 2 at a front side 4 and provided with stud bumps 6, and a further wiring layer 8 embedded in the dielectric 2 at a rear side 7 opposite to the front side 4. The dielectric 2 may comprise an oxide of the semiconductor material, for instance, particularly silicon dioxide, and/or a nitride of the semiconductor material, particularly $Si_3N_4$. The dielectric 2 may be a passivation formed from any suitable passivating dielectric material.

The through-substrate vias 3 are formed by metallizations, which are applied to sidewalls of via holes in the substrate 1. The cores of the through-substrate vias 3 can be free from the metallizations and left void, or they may be filled with a further material, which may be electrically conductive or insulating. The appended FIGURE shows the through-substrate vias 3 filled with the dielectric 2, but in other embodiments the inner volume of the through-substrate vias 3 may be void, and their sidewall metallizations may be covered by a thin protecting and/or insulating layer, for example.

The conductor layers, which are designated as wiring layer 5 and further wiring layer 8, may be any structured metal layer or a plurality of metal layers arranged on different metallization levels. If there are two or more metallization levels, the dielectric 2 may be provided as an intermetal dielectric. The conductor layers may include the wiring of an integrated circuit, which may especially comprise CMOS devices arranged at the front side 4 or at the rear side 7, and/or a redistribution layer, for example.

The stud bumps 6 are shown by way of example and can be substituted with any contact connections suitable for external electrical terminals. If the stud bumps 6 are formed by solder balls, they may be provided with an under-bump metallization, which is applied as an additional thin layer according to standard semiconductor technology and is hence not shown in the FIGURE. The conductors on the opposite sides of the substrate 1 are interconnected by means of the through-substrate vias 3.

An integrated sensor, which may especially be a gas sensor, comprises a sensor layer 21 arranged in or on the substrate 1 without mounting a separate sensor chip. For improved thermal isolation recesses 22 may be formed in the substrate 1 below the sensor layer 21. An electrical connection between the sensor layer 21 and the further wiring layer 8 and/or the through-substrate via 3 may be provided by vertical interconnects or plugs 23 leading through the dielectric 2. If the further wiring layer 8 is arranged contiguous to the sensor layers 21, especially overlapping as shown in the FIGURE, and without interspace between the layers in the vertical direction, a direct electric contact between the further wiring layer 8 and the sensor layer 21 may be formed without vertical interconnects or plugs. A hot plate 24 is integrated in or on the substrate 1 in the vicinity of the sensor layer 21. The hot plate 24 may be a resistive heater, which is heated by an electric current, and may be formed as a conductor track having an appropriate resistance. The cavity 17 is formed above the sensor layer 21 within the mold compound 14 and is closed by the membrane 15. It may be favorable if the membrane 15 is impermeable to liquids. In case of a gas sensor, the membrane 15 is permeable at least to the gas that is to be detected. In particular, the membrane 15 may be polytetrafluoroethylene (PTFE) or expanded polytetrafluoroethylene (ePTFE), for instance.

In the method of production, a mold compound 14 is applied above the rear side 7 of the substrate 1. The mold compound 14 is structured into compartments, which are enclosed by posts or walls formed by the mold compound 14. A plurality of sensor layers are thus arranged in the compartments of the mold compound 14. The application and structuring of the mold compound 14 may be facilitated by a film assisted molding process, which is known per se. It may be favorable to cover the membrane temporarily with a protection film, especially if further process steps are performed that are liable to poison the sensor layers or otherwise adversely affect the components, like a solder reflow process, for example. The protection film is afterwards removed, whereas the membrane 15 is provided as a permanent cover or protection, especially for sealing the cavity up to prevent water from entering. The substrate 1 is divided into individual semiconductor devices by a wafer dicing process. The stud bumps 6 can then be used as terminals for an external electric connection of the sensors.

When the wafer-level package has been formed by the mold compound and the membrane, the individual semiconductor devices are separated by wafer dicing, cutting through the substrate and through the walls that are formed by the mold compound.

The invention claimed is:

1. A semiconductor sensor device, comprising:
   a substrate of semiconductor material with a front side and an opposite rear side;
   a wiring layer at the front side;
   a further wiring layer at the rear side;
   a through-substrate via connecting the wiring layer and the further wiring layer;
   a sensor layer arranged at the rear side and electrically connected with the further wiring layer;
   a mold compound arranged on the rear side, the mold compound being covered with a membrane, the mold compound and the membrane forming a cavity accommodating the sensor layer; and
   a hot plate being arranged on or in the substrate in the vicinity of the sensor layer,
   wherein the sensor layer is arranged above the substrate and the hot plate is arranged between the substrate and the sensor layer,
   wherein the membrane is impermeable to liquids and permeable to a gas,
   wherein the sensor layer is provided for a gas sensor,
   wherein a recess is formed in the substrate below the sensor layer, and the hot plate is arranged above the recess of the substrate, and
   wherein the hot plate is part of the further wiring layer, which is a structured metal layer arranged in an oxide or nitride of the semiconductor material.

2. The semiconductor device according to claim 1, wherein the membrane is polytetrafluoroethylene or expanded polytetrafluoroethylene.

3. A method of producing semiconductor devices, comprising:
   forming a plurality of semiconductor devices on a substrate of semiconductor material with a front side and an opposite rear side;
   arranging a wiring layer at the front side;
   arranging a further wiring layer at the rear side;

forming through-substrate vias connecting the wiring layer and the further wiring layer;

arranging a plurality of hot plates and sensor layers at the rear side;

arranging a mold compound on the rear side above the substrate, the mold compound being structured to form a plurality of cavities for the accommodation of the sensor layers; and covering the cavities with a membrane, wherein the membrane is impermeable to liquids and permeable to a gas, wherein the sensor layers are provided for at least one gas sensor, wherein at least one recess is formed in the substrate below the sensor layers, and the hot plates are arranged above the at least one recess of the substrate, and wherein the hot plates are part of the further wiring layer, which is a structured metal layer arranged in an oxide or nitride of the semiconductor material.

4. The method according to claim 3, wherein the membrane is polytetrafluoroethylene or expanded polytetrafluoroethylene.

5. The method according to claim 3, wherein the membrane is temporarily covered with a protection film enabling a solder reflow process without poisoning the sensor layers.

6. The method according to claim 3, wherein the membrane is glued to the mold compound.

7. The method according to claim 3, wherein the membrane is ultrasonically welded to the mold compound.

8. The method according to claim 3, wherein the mold compound is applied in a structured fashion by use of a film assisted molding process.

9. A semiconductor sensor device, comprising:

a substrate of semiconductor material;

a sensor layer arranged above the substrate;

a mold compound arranged above the sensor layer, the mold compound forming a cavity accommodating the sensor layer;

a membrane covering the mold compound; and a hot plate arranged on or in the substrate in the vicinity of the sensor layer, wherein the sensor layer is arranged above the substrate and the hot plate is arranged between the substrate and the sensor layer, wherein the membrane is impermeable to liquids and permeable to a gas, wherein the sensor layer is provided for a gas sensor, wherein a recess is formed in the substrate below the sensor layer, and the hot plate is arranged above the recess of the substrate, and wherein the hot plate is part of the further wiring layer, which is a structured metal layer arranged in an oxide or nitride of the semiconductor material.

* * * * *